(12) United States Patent
Maiorino et al.

(10) Patent No.: US 8,590,588 B2
(45) Date of Patent: Nov. 26, 2013

(54) SYSTEM AND METHOD FOR MAKING TAPERED LOOPED SUTURE

(75) Inventors: Nicholas Maiorino, Branford, CT (US); Timothy Kosa, Milford, CT (US); Mark Buchter, Orange, CT (US); Keith Kroeber, Portland, CT (US); Richard Casey Hart, Clinton, CT (US)

(73) Assignee: Covidien LP, Mansfield, MA (US)

( * ) Notice: Subject to any disclaimer, the term of this patent is extended or adjusted under 35 U.S.C. 154(b) by 494 days.

(21) Appl. No.: 12/751,456

(22) Filed: Mar. 31, 2010

(65) Prior Publication Data

US 2010/0276062 A1 Nov. 4, 2010

Related U.S. Application Data

(60) Provisional application No. 61/173,719, filed on Apr. 29, 2009.

(51) Int. Cl.
*B32B 37/00* (2006.01)

(52) U.S. Cl.
USPC .............................. 156/378; 156/510; 156/581

(58) Field of Classification Search
USPC ................. 156/378, 510, 530, 538, 539, 580, 156/580.1, 580.2, 581
See application file for complete search history.

(56) References Cited

U.S. PATENT DOCUMENTS

| | | |
|---|---|---|
| 2,514,184 A | 7/1950 | Lower |
| 3,311,110 A | 3/1967 | Sol et al. |
| 3,513,848 A | 5/1970 | Winston et al. |
| 3,657,056 A | 4/1972 | Winston et al. |
| 3,874,963 A | 4/1975 | Barger |
| 4,575,372 A * | 3/1986 | Gundersen .................. 623/1.41 |
| 4,662,068 A | 5/1987 | Polonsky |
| 4,838,964 A * | 6/1989 | Thomsen et al. ............ 156/73.1 |
| 4,950,285 A | 8/1990 | Wilk |
| 5,059,212 A | 10/1991 | Kortoff |
| 5,226,535 A | 7/1993 | Rosdhy et al. |
| 5,259,846 A | 11/1993 | Granger et al. |
| 5,383,905 A | 1/1995 | Golds et al. |
| 5,403,331 A | 4/1995 | Chesterfield et al. |
| 5,417,700 A | 5/1995 | Egan et al. |
| 5,865,836 A | 2/1999 | Miller |
| 5,893,880 A | 4/1999 | Egan et al. |
| 5,937,504 A * | 8/1999 | Esteves et al. ............... 29/564.6 |
| 6,077,277 A | 6/2000 | Mollenauer et al. |

(Continued)

FOREIGN PATENT DOCUMENTS

| | | |
|---|---|---|
| EP | 0 444 777 A1 | 9/1991 |
| EP | 0 490 143 A2 | 6/1992 |

(Continued)

OTHER PUBLICATIONS

European Search Report for EP 10 25 0847 date of completion is Aug. 25, 2010 (3 pages).

(Continued)

*Primary Examiner* — James Sells (57) ABSTRACT

A system for forming a looped suture is provided. The system includes a suture supply assembly configured for supplying thread, a flipper gripping assembly configured for forming a loop in the thread, a carriage assembly configured for advancing the thread through the forming process, and a welding assembly configured for securing the loop in the thread.

12 Claims, 6 Drawing Sheets

(56) References Cited

U.S. PATENT DOCUMENTS

| | | |
|---|---|---|
| 6,089,438 A | 7/2000 | Suzuki |
| 6,174,324 B1 | 1/2001 | Egan et al. |
| 6,217,591 B1 | 4/2001 | Egan et al. |
| 6,286,746 B1 | 9/2001 | Egan et al. |
| 6,296,659 B1 | 10/2001 | Foersteer |
| 6,358,271 B1 | 3/2002 | Egan et al. |
| 6,368,343 B1 | 4/2002 | Bonutti et al. |
| 6,409,743 B1 | 6/2002 | Fenton, Jr. |
| 6,488,690 B1 | 12/2002 | Morris et al. |
| 6,669,705 B2 | 12/2003 | Westhaver et al. |
| 6,767,426 B1 * | 7/2004 | Yamamoto .............. 156/270 |
| 7,090,111 B2 | 8/2006 | Egan et al. |
| 7,429,266 B2 | 9/2008 | Bonutti et al. |
| 7,533,791 B2 | 5/2009 | Steiner et al. |
| 7,582,097 B2 | 9/2009 | McRury et al. |
| 2002/0029065 A1 | 3/2002 | Shchervinsky |
| 2004/0122451 A1 | 6/2004 | Wood |
| 2005/0165448 A1 | 7/2005 | Egan et al. |
| 2006/0025858 A1 | 2/2006 | Alameddine |
| 2006/0259076 A1 | 11/2006 | Burkhart et al. |
| 2009/0216269 A1 | 8/2009 | Harington et al. |
| 2009/0248070 A1 | 10/2009 | Kosa et al. |
| 2009/1259251 | 10/2009 | Cohen |
| 2010/1010170 | 4/2010 | Maiorino et al. |
| 2011/0180196 A1 | 7/2011 | Hart et al. |
| 2012/0024482 A1 | 2/2012 | Maiorino et al. |

FOREIGN PATENT DOCUMENTS

| | | |
|---|---|---|
| EP | 2 184 157 A1 | 5/2010 |
| FR | 2729940 | 8/1996 |
| WO | WO96/25109 | 8/1996 |
| WO | WO99/26542 | 6/1999 |
| WO | WO00/30550 A1 | 6/2000 |
| WO | WO 02/22025 A1 | 3/2002 |
| WO | WO2005/087113 A1 | 9/2005 |

OTHER PUBLICATIONS

European Search Report EP 10 25 1270 date of completion Feb. 8, 2012.

European Search Report EP 12163323.4-2310 date of completion Jul. 25, 2012.

European Search Report EP 12195006.7-2310 date of completion Jan. 30, 2013.

International Search Report PCT/US2013/042340 dated Aug. 27, 2013.

* cited by examiner

SYSTEM AND METHOD FOR MAKING TAPERED LOOPED SUTURE

CROSS-REFERENCE TO RELATED APPLICATION

The present application claims benefit of and priority to U.S. Provisional Application Ser. No. 61/173,719, filed Apr. 29, 2009, entitled "System and Method for Making Tapered Looped Suture", the entire contents of which are incorporated herein in its entirety.

BACKGROUND

1. Technical Field

The present disclosure relates to a system of forming a looped suture. More particularly, the present disclosure relates to an automated system of forming a looped suture having a taper cut.

2. Background of Related Art

Sutures including loops formed therein are known. A loop may be formed in a suture for a number of reasons. A loop formed in a suture during manufacture may be used to secure the suture to tissue. In this manner, once the non-looped end of the suture is inserted through tissue, that end may be threaded through the loop to form a slip knot-like configuration that may be tied to secure tissue. In another application, a loop may be formed in a suture in place of a knot. This requires the use of a handheld instrument that may be brought into an operating room.

Regardless of the reason for forming the loop, when a loop is formed in a suture, whether using adhesive, heat or ultrasonic energy, the diameter of the suture is doubled where the two suture portions overlap. In the event that the suture loop is used to secure tissue, the doubling of the diameter of the suture in order to create the loop increases the amount of force necessary to pull the loop through tissue. This increased force applied to the suture may result in tearing or other unnecessary trauma to the tissue being sutured. Therefore, it would be beneficial to have a system and method of forming a looped suture to include a taper cut.

SUMMARY

According, a system for forming a looped suture is provided. The system includes a suture supply assembly configured for supplying thread, a flipper gripping assembly configured for forming a loop in the thread, a carriage assembly configured for advancing the thread through the forming process, and a welding assembly configured for securing the loop in the thread.

The system may further include a cutter assembly for severing the thread upon completion of the loop forming process and/or a trimming assembly configured for forming a tapered cut in the thread. The system may also include an initial gripping assembly positioned between the suture supply assembly and the flipper gripping assembly, the initial gripping assembly being configured for selectively gripping the thread throughout the forming process and/or a thread lengthening assembly configured for extending the length of the thread. In one embodiment, the system includes a monitoring assembly configured for monitoring the forming process. The flipper gripping assembly may include a mandrel upon which the thread is wrapped about. The carriage assembly may include a hook assembly configured to engage the thread.

Also provided is a method of forming a looped suture. The method includes the steps of providing a first end a thread from a spool of thread to a flipper gripping assembly, wherein the flipper gripping assembly includes a mandrel having a slot formed therein, receiving a hook from a carriage assembly with the slot formed in the mandrel, wrapping the first end of the of the thread about the mandrel such that the thread is positioned over the slot, retracting the hook from within the slot formed in the mandrel to form a loop about the hook, wherein the first end of the thread is received adjacent a body portion of the thread distal of the loop, and welding the first end of the thread to the adjacent body portion of the thread distal of the loop.

The method forming a looped suture may further include the step of cutting a tapered surface into the first end of the thread and/or selectively gripping the body portion of the thread to provide tension to the thread. The welding may be ultrasonic. The method may also include the steps of cutting the body portion of the thread to length and/or lengthening the body portion of thread prior to cutting the body portion.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
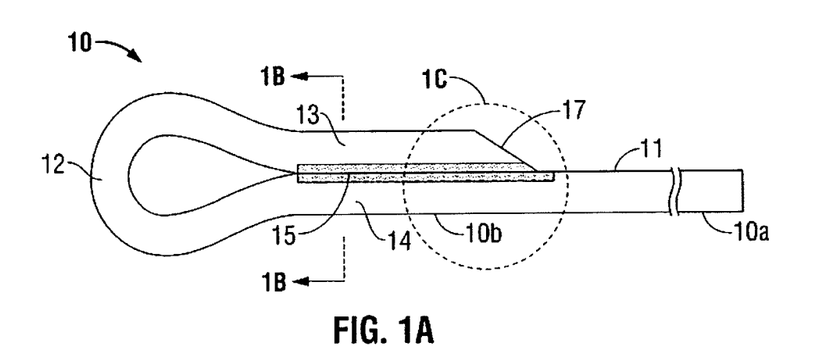
FIG. 1A is a side view of a looped suture including a tapered portion.

A system and method for forming a looped suture including a tapered cut is herein described. Referring initially to FIG. 1A, a looped suture formed in accordance with the method of the present disclosure is shown generally as looped suture 10. Suture 10 is formed from a monofilament thread 11, however, it is envisioned that suture 10 may be formed braided threads, multifilament threads and other surgical fibers. Although shown having a circular cross-sectional geometry, the cross-sectional geometry of thread 11 may be of any suitable shape. For example, thread 11 may be round, elliptical, square, flat, octagonal, and rectangular. Thread 11 may be formed of degradable materials, non-degradable materials, and combinations thereof. Thread 11 may be formed using any technique within the purview of those skilled in the art, such as, for example, extrusion, molding and/or gel spinning.

Figure 1B:
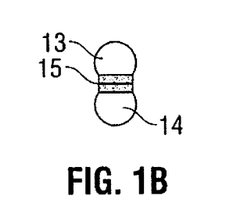
FIG. 1B is a cross-sectional end view of the looped suture of FIG. 1A, taken along line 1B-1B.
Figure 1C:
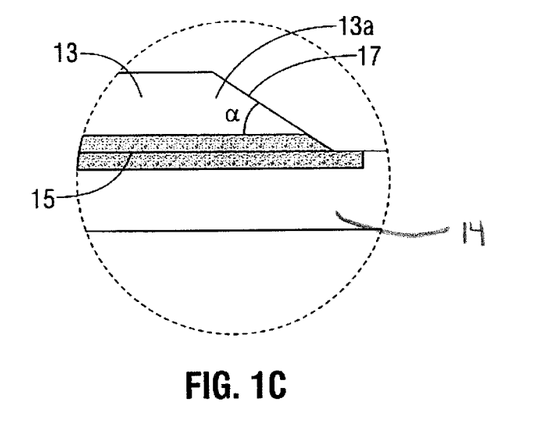
FIG. 1C is an enlarged side view of portion 1C of FIG. 1A.

With reference to FIGS. 1A-1C, looped suture 10 includes a loop 12 formed on a distal end 10b thereof. Loop 12 forms a substantially teardrop shape and may be formed of any size.

A first section 13 of monofilament thread 11 overlays a second section 14 of thread 11 to form loop 12. The adjacent surfaces of first and second sections 13, 14 form a joined segment or joint 15. As shown, joined segment 15 extends beyond first section 13 of thread 11. In this manner, first and second sections 13, 14 of thread 11 are less likely to separate or peel away from each other as looped suture 10 is pulled through tissue (not shown).

As will be described in further detail below, first and second sections 13, 14 of thread 11 are welded together to form joined segment 15. In this manner, first and second sections 13, 14 of thread 11 are locally heated until each fuses to form joined segment 15. Various types of energy may be used to locally heat first and second sections 13, 14 to form joined segment 15, including, radiofrequency (RF), ultrasonic, laser, electrical arc discharge, and thermal. Alternatively, first and second sections 13, 14 of thread 11 may be joined using glue, epoxy or other adhesive.

With particular reference to FIG. 1C, a proximal end 13a of first section 13 is angled to form a tapered surface 17. Tapered surface 17 angles downwardly towards proximal end 10a (FIG. 1A) of looped suture 10. Tapered surface 17 may form an angle between zero degrees)(0° and ninety degrees)(90°, and preferably between about fifteen degrees)(15° to about sixty degrees)(60°. Tapered surface 17 facilitates insertion of loop 12 into or through tissue. Tapered surface 17 may be formed prior to, during or following the joining of first and second sections 13, 14.

Although shown having a substantially planar taper, tapered surface 17 may include any number of configurations. For example, tapered surface 17 may be beveled, may include a laterally and longitudinally concave taper, may include a laterally and longitudinally convex taper, or may include any combination thereof. Tapered surface 17 may be selected depending on the tissue being sutured and/or the depth loop 12 is desired to be received within the tissue.

Figure 2:
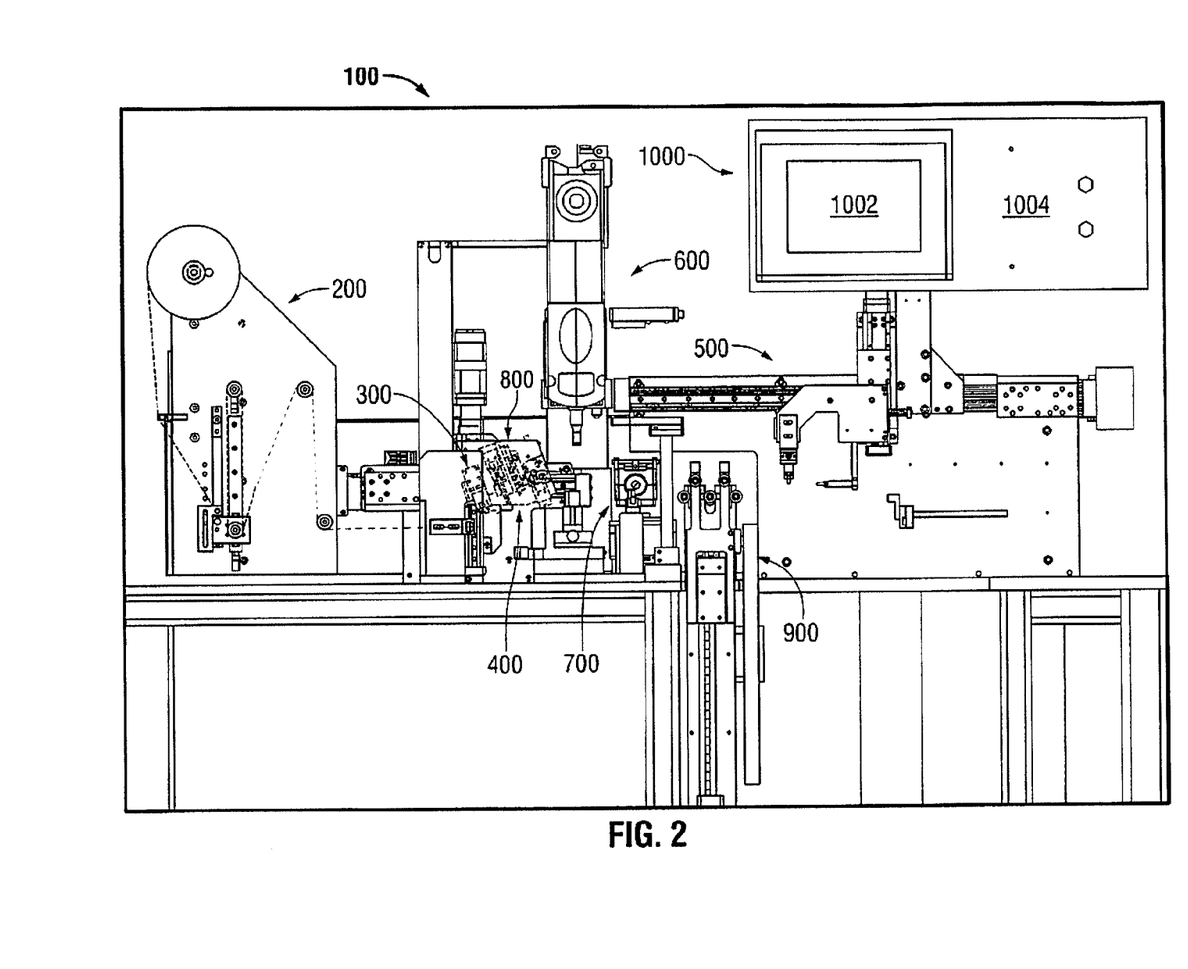
FIG. 2 is a side view of tapered loop forming system of the present disclosure.

A system for forming loop 12 on distal end 10b of looped suture 10 will now be described with reference to FIGS. 2-6B, and is shown generally as tapered loop forming system 100. Although shown as being automated, it is envisioned that various components and/or process within tapered loop forming system 100 may be manually completed. Referring initially to FIG. 2, system 100 includes a suture supply assembly 200, an initial gripping assembly 300, a flipper gripping assembly 400, a carriage assembly 500, a welding assembly 600, a trimming assembly 700, a cutter assembly 800, and may optionally include a thread lengthening assembly 900 and a monitoring assembly 1000.

Figure 3:
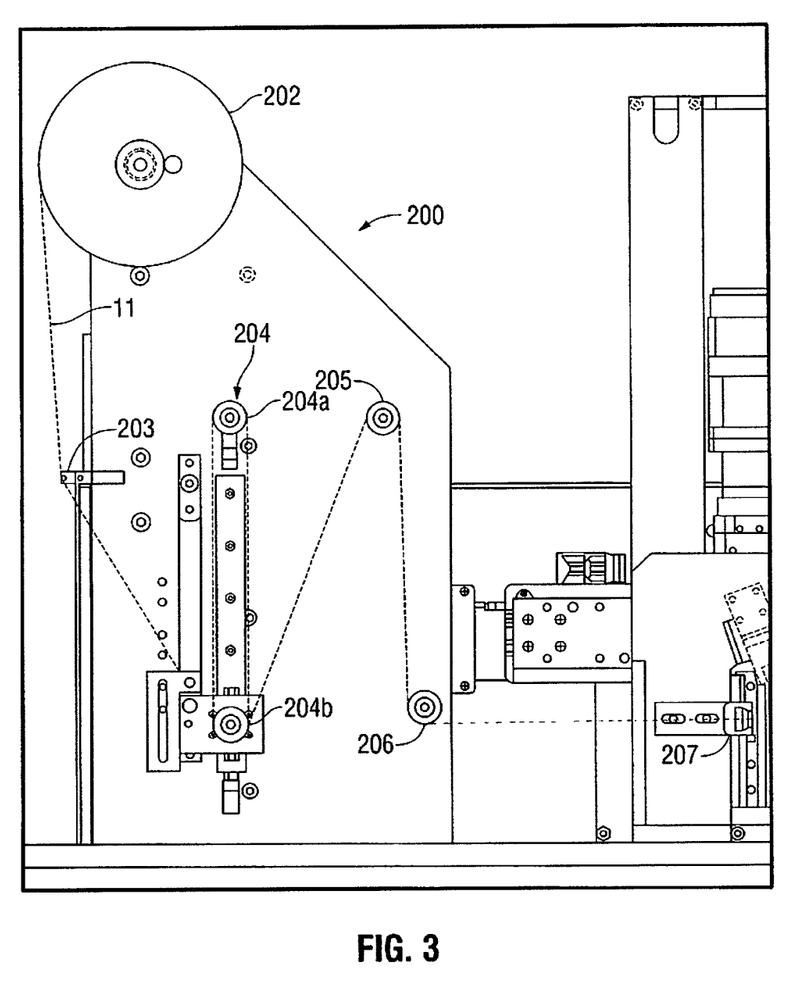
FIG. 3 is an enlarged side view of a suture supply assembly of the tapered loop forming system of FIG. 2.

With reference now to FIG. 3, supply assembly 200 is configured to provide thread 11 to initial gripping assembly 300 (FIG. 2). Supply assembly 200 includes a spool 202, a first guide member 203, a roller assembly 204, first and second rollers 205, 206 and a second guide member 207. First guide member 203 is configured to direct thread 11 from spool 202 to roller assembly 204. Roller assembly 204 includes a set of fixed rollers 204a and a set of adjustable rollers 204b. Roller assembly 204 is configured to receive thread 11 about fixed and adjustable rollers 204a, 204b a plurality of times. As shown, rollers 204a, 204b are configured to receive thread 11 thereabout four (4) times, however, roller assembly 204 may be configured to receive thread 11 thereabout more or less than four times. First and second rollers 205, 206 are positioned to direct thread 11 through second guide member 207. Although shown including supply assembly 200 for providing a continuous supply of thread 11 from spool 202, alternative supply assemblies are know and may be modified for use with system 100. For example, thread 11 may be provided in fixed or predetermined lengths rather than continuously from a spool. In this manner, the aspects of the present disclosure should not be read as limited to the supply assembly herein disclosed.

Figure 4:
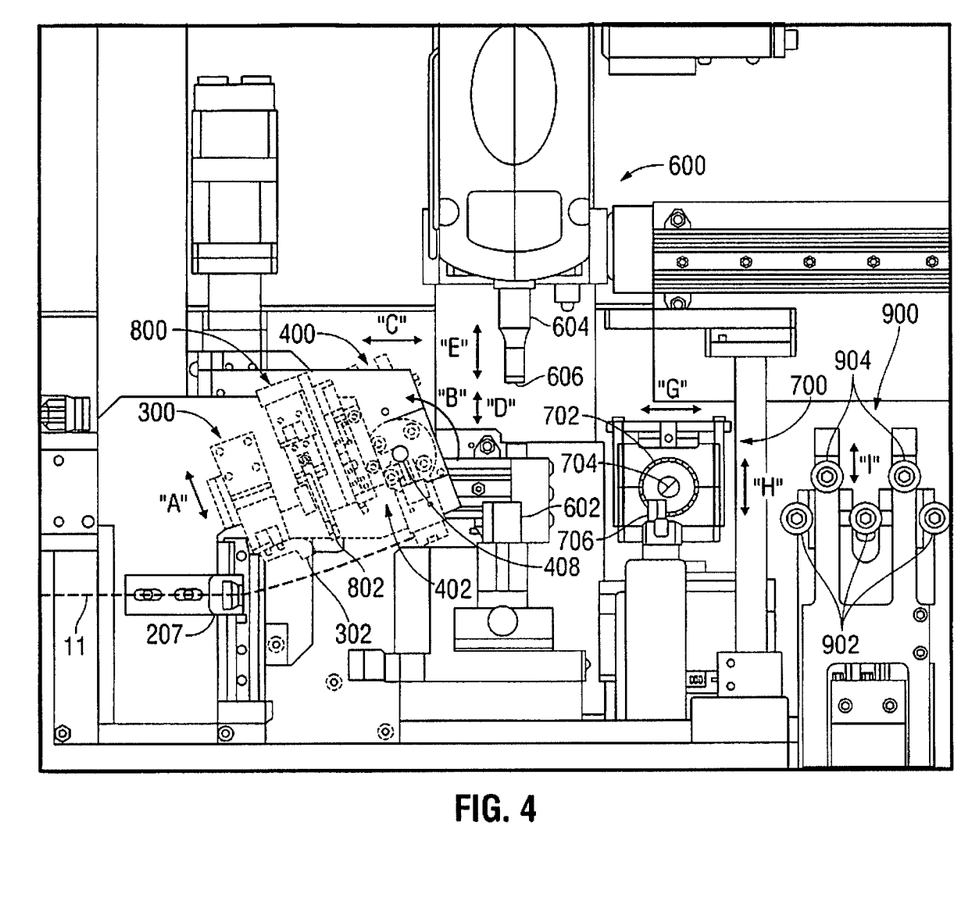
FIG. 4 is an enlarged sectional side view of the tapered loop forming system of FIG. 2.

Turning now to FIG. 4, initial gripping assembly 300 includes an initial gripper 302 configured to selectively engage and selectively grasp thread 11 throughout the looped end forming process. Initial gripping assembly 300 translates on a diagonal, in the direction of arrows "A". During the looped end forming process, initial gripping assembly 300 is activated to grasp a proximal end of thread 11 when tension is applied to a distal end of thread 11 to prevent excess thread from being pulled from supply assembly 200. In this manner, initial gripping assembly 300 may include any device or apparatus capable of selectively grasping thread 11.

Figure 5:
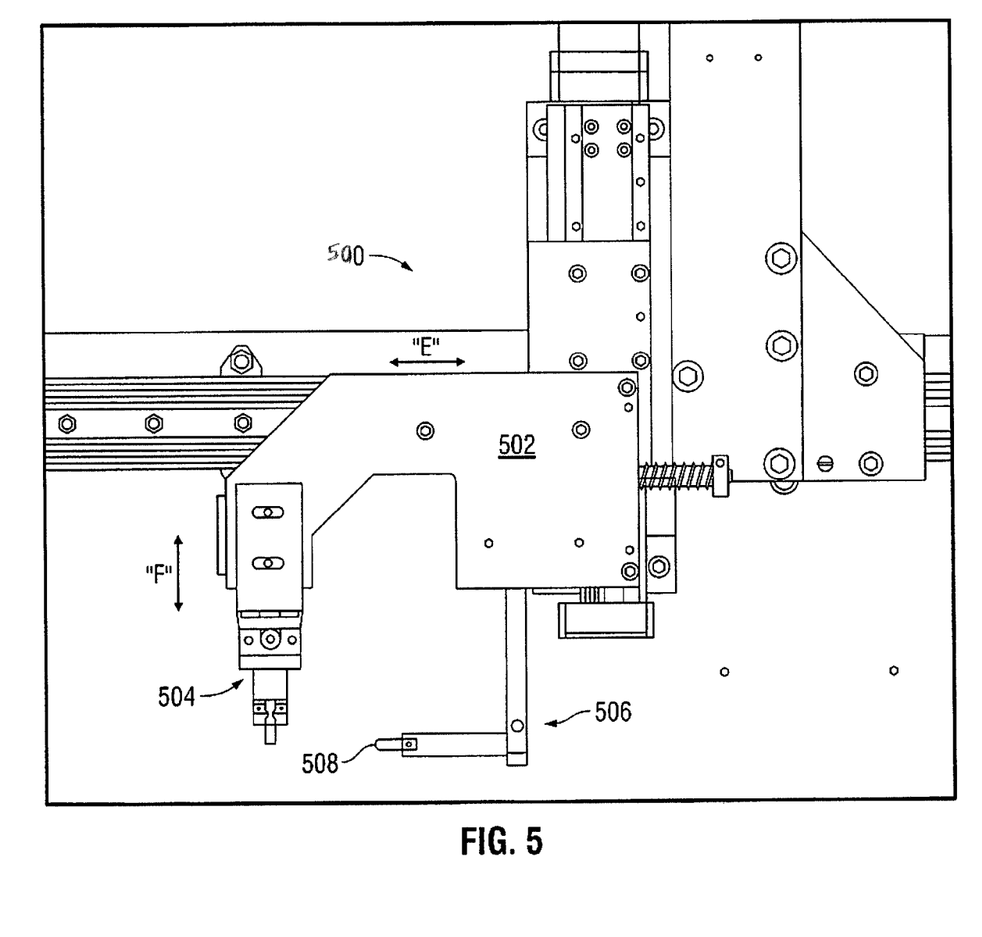
FIG. 5 is an enlarged side view of carriage assembly of the tapered loop forming system of FIG. 2.

With reference still to FIG. 4, flipper gripping assembly 400 is configured to create loop 12 in thread 11. Gripping assembly 400 includes a rotating gripper 402 configured to selectively grasp a first end of thread 11. A mandrel 408 extends from rotating gripper 402 and includes a slot (not shown) configured to receive a hook 508 from carriage assembly 500 (FIG. 5). Rotating gripper 402 is configured to rotate relative to mandrel 408, in the direction of arrow "B", to loop thread 11 around mandrel 408. Flipper gripping assembly 400 is configured to move horizontally, in the direction of arrows "C", and vertically, in the direction of arrows "D".

With reference now to FIG. 5, carriage assembly 500 is configured to translate thread 11 through the loop forming process. Carriage assembly 500 includes a support member 502 having a tag end gripper 504 and a hook assembly 506. A hook 508 extends from hook assembly 506 and is configured to receive thread 11 thereabout. Carriage assembly 500 optionally includes a tensioning cylinder (not shown) for tensioning thread 11 with a predetermined force to test the strength of weld 15 (FIG. 1B). Carriage assembly 500 is configured to move horizontally, in the direction of arrows "E", and vertically, in the direction of arrows "F".

Figure 6A:
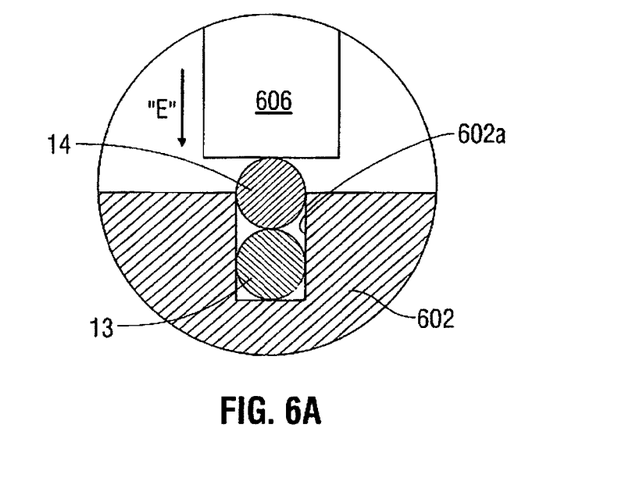
FIG. 6A is an enlarged cross-sectional side view of welding assembly of the loop forming system of FIG. 2, in a partially activated position.
Figure 6B:
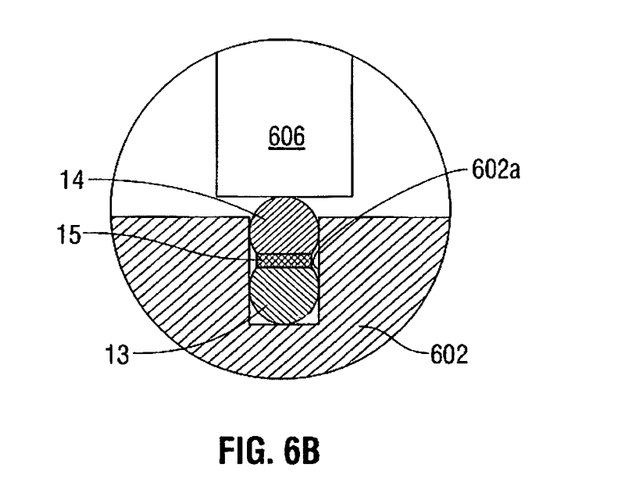
FIG. 6B is an enlarge cross-sectional side view of the welding assembly of FIG. 6A, in a fully activated position.

With reference back to FIG. 4, welding assembly 600 is configured to weld joint 15 in thread 11 to form loop 12. Welding assembly 600 includes an anvil 602 and an ultrasonic horn 604. With reference to FIGS. 6A and 6B, in one embodiment, ultrasonic horn 604 includes a flat die 606 configured to engage first section 13 of thread 11 during the welding process. As shown, anvil 602 defines a channel 602a configured to receive the entire width of second section 14 and more than half the width of first section 13 of thread 11. In an alternative embodiment, die 606 includes a channel (not shown) for receiving at least a portion of first section 13 of thread 11.

Still referring to FIG. 4, trimming assembly 700 is configured to cut tapered surface 17 of looped end portion 12. Trimming assembly 700 includes an ultrasonic horn 704 having a trimming blade 702. Trimming assembly 700 further includes a gripping anvil 706 for gripping thread 11 as trimming blade 702 engages thread 11. Trimming assembly 700 is configured to move horizontally, in the direction of arrows "G", and vertically, in the direction of arrows "H". The rate at which trimming assembly 700 is moved horizontally and vertically affects the configuration of cut tapered surface 17. Trimming assembly 700 is further configured to be advanced and retracted. In one embodiment, trimming blade 702 is configured to be rotated one-hundred and eighty degrees (180°) such that both cutting surface thereof may be used. Although shown adapted for use as an ultrasonic cutter, trimming assembly 700 may be configured cut tapered surface 17 without the use of ultrasonic energy. In one embodiment, a laser is used to cut tapered surface 17. Alternatively, trimming blade 702 may be heated to assisted in the cutting of thread 11.

With continued reference to FIG. 4, cutter assembly 800 is configured to cut thread 11 upon completion of the looped end forming process. Cutter assembly 800 includes a cutting blade 802. Cutter assembly 800 is configured to move parallel to initial gripper assembly 300, in the direction of arrows "A". Cutter assembly 800 is configured to cut thread 11 once thread 11 has attained an appropriate length. Cutter assembly 800 may be configured to cut a straight or tapered end on a proximal end 10a (FIG. 1A) of suture 10.

With reference to FIGS. 2 and 4, lengthening assembly 900 is configured to increase the length of thread 11 prior to thread 11 being cut by cutter assembly 800. As shown, lengthening assembly 900 includes a set of fixed rollers 902 and a set of adjustable rollers 904. Although shown including three and two rollers, respectively, sets of fixed and adjustable rollers 902, 904 may include any number of rollers. When thread 11 is received between fixed and adjustable rollers 902, 904, movement of adjustable rollers 904 relative to fixed rollers 902, in the direction of arrows "I", causes thread 11 to lengthen. The greater the number of rollers 902, 904, the less relative movement between rollers 902, 904 is necessary to lengthen thread 11.

Monitoring assembly 1000 is configured to monitor the various steps of the looped end forming process. Monitoring assembly 1000 includes a screen 1002 and a control panel 1004.

The operation of forming station 100 will now be described with reference to FIG. 2-6B. Thread 11 extends from spool 202 through first guide member 203 before being received about roller assembly 204. Thread 11 is wrapped around fixed rollers 204a and adjustable rollers 204b of roller assembly 204 four times, and is then received about first and second rollers 205, 206 before being received through second guide member 207.

Thread 11 extends through second guide member 207 where it is grasped by initial gripper 302 prior to being grasped by rotating gripper 402. Initial gripper 302 then releases thread 11 and flipper gripping assembly 400 translates towards anvil 602 of welding assembly 600 as carriage assembly 500 translates towards anvil 602 from the opposite direction. Flipper gripping assembly 400 and carriage assembly 500 are configured such that as carriage assembly 500 nears flipper gripping assembly 400, hook 508 of hook assembly 506 is received in the slot (not shown) of mandrel 408. Once hook 508 is received within the slot, rotating gripper 402 rotates, in the direction of arrow "B", to loop thread 11 about mandrel 408. Flipper gripping assembly 400 and carriage assembly 500 then move to position first and second sections 13, 1514 of thread 11 within channel 602a of anvil 602 (FIG. 6A). As carriage assembly 500 approximates away from flipper gripping assembly 400, hook 508 extends from within the slot formed in mandrel 408 with thread 11 received thereabout.

Once first and second sections 13, 14 of thread 11 are received with channel 602a (FIG. 6A) of anvil 602, ultrasonic horn 604 is activated and flat die 606 is approximate towards anvil 602, in the direction of arrow "E". Engagement of die 606 with first section 13 of thread 11 causes first and second sections 13, 14 to weld together to form joined segment 15 (FIG. 1B). Upon completion of the welding of first and second sections 13, 14, tag end gripper 504 grips the tag end (not shown) of thread 11 and rotating gripper 402 releases thread 11.

Carriage assembly 500 then moves to position welded first and second section 13, 14 of thread 11 within gripping anvil 706 of trimming assembly 700. Gripping anvil 706 maintains thread 11 as blade 704 of ultrasonic horn 702 is moved to cut tapered surface 17 (FIG. 1A) into first section 13 of thread 11. Gripping anvil 706 then releases thread 11 and carriage assembly 500 continues to translate away from supply assembly 200 to extend the length of thread 11. Cutting assembly 800 is then activated to cut thread 11. Prior to the cutting of thread 11, tension is applied to loop 12 (FIG. 1A) of thread 11 by the tensioning cylinder (not shown) located within carriage assembly 500 to test the strength of weld 15. Optionally, thread 11 may engage lengthening assembly 900 to extend the length of thread 11 prior to cutting.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that system 100 may include more than one welding assembly 600 and trimming assembly 700 to produce more than one suture 10 per activation.

What is claimed is:

1. A system for forming a looped suture, the system comprising:
   a suture supply assembly configured for supplying thread;
   a flipper gripping assembly configured for forming a loop in the thread;
   a carriage assembly configured for advancing the thread through the forming process;
   a welding assembly configured for securing the loop in the thread; and
   a trimming assembly configured for forming a tapered cut in the thread, the trimming assembly being configured to move in a first horizontal direction and in a second vertical direction, wherein rates of movement of the trimming assembly in the first and second directions affects the configuration of the tapered cut in the thread.

2. The system of claim 1, further including a cutter assembly for severing the thread upon completion of the loop forming process.

3. The system of claim 1, further including an initial gripping assembly positioned between the suture supply assembly and the flipper gripping assembly, the initial gripping assembly being configured for selectively gripping the thread throughout the forming process.

4. The system of claim 1, further including a thread lengthening assembly configured for extending the length of the thread.

5. The system of claim 1, further including a monitoring assembly configured for monitoring the forming process.

6. The system of claim 1, wherein the flipper gripping assembly includes a mandrel upon which the thread is wrapped about.

7. The system of claim 1, wherein the carriage assembly includes a hook assembly configured to engage the thread.

8. The system of claim 6, wherein the carriage assembly includes a hook assembly configured to engage the thread and the mandrel defines a slot configured to receive a portion of the hook assembly.

9. The system of claim 1, wherein the suture supply assembly includes a spool, first and second guide members, a roller assembly, and first and second rollers.

10. The system of claim 9, wherein the first guide member is configured to direct the thread from the spool to the roller assembly.

11. The system of claim 9, wherein the roller assembly includes a set of fixed rollers and a set of adjustable rollers.

12. The system of claim 9, wherein the first and second rollers are configured to direct the thread through the second guide member.

* * * * *